United States Patent [19]
Kohayakawa

[11] Patent Number: 5,903,336
[45] Date of Patent: *May 11, 1999

[54] EYE EXAMINING APPARATUS HAVING A DRIVER FOR DRIVING AN EYE EXAMINING SYSTEM

[75] Inventor: Yoshimi Kohayakawa, Yokohama, Japan

[73] Assignee: Canon Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/788,349

[22] Filed: Jan. 27, 1997

Related U.S. Application Data

[63] Continuation of application No. 08/378,579, Jan. 26, 1995, abandoned.

[30] Foreign Application Priority Data

Jan. 28, 1994 [JP] Japan .................................. 6-026042

[51] Int. Cl.⁶ ...................................................... A61B 3/00
[52] U.S. Cl. ............................................. 351/245; 351/208
[58] Field of Search .................................... 351/200, 205, 351/208, 209, 245; 359/458

[56] References Cited

U.S. PATENT DOCUMENTS

| | | | |
|---|---|---|---|
| 4,078,854 | 3/1978 | Yano | 359/458 |
| 4,697,895 | 10/1987 | Sekiguchi et al. | 351/243 |
| 5,037,194 | 8/1991 | Kohayakawa et al. | 351/224 |
| 5,098,426 | 3/1992 | Sklar et al. | 351/209 |
| 5,144,346 | 9/1992 | Nakamura et al. | 351/208 |
| 5,231,430 | 7/1993 | Kohayakawa | 351/243 |
| 5,237,351 | 8/1993 | Kohayakawa et al. | 351/243 |
| 5,325,135 | 6/1994 | Nakamura et al. | 351/205 |
| 5,337,095 | 8/1994 | Katsuragi et al. | 351/208 |
| 5,349,415 | 9/1994 | Nishida | 354/432 |

*Primary Examiner*—Huy Mai
*Attorney, Agent, or Firm*—Fitzpatrick, Cella, Harper & Scinto

[57] ABSTRACT

An eye examining apparatus includes an eye examining system provided with an image pickup device for picking up the image of an eye to be examined and for examining the eye to be examined, a driver for driving the eye examining system, an input device for permitting an operator to effect an input operation to operate the driver a display for displaying the image of the eye to be examined obtained by the image pickup device, and a controller for changing the relation between the direction of the input to the input device and the direction of driving of the driver conforming thereto in conformity with the direction of the display.

19 Claims, 2 Drawing Sheets

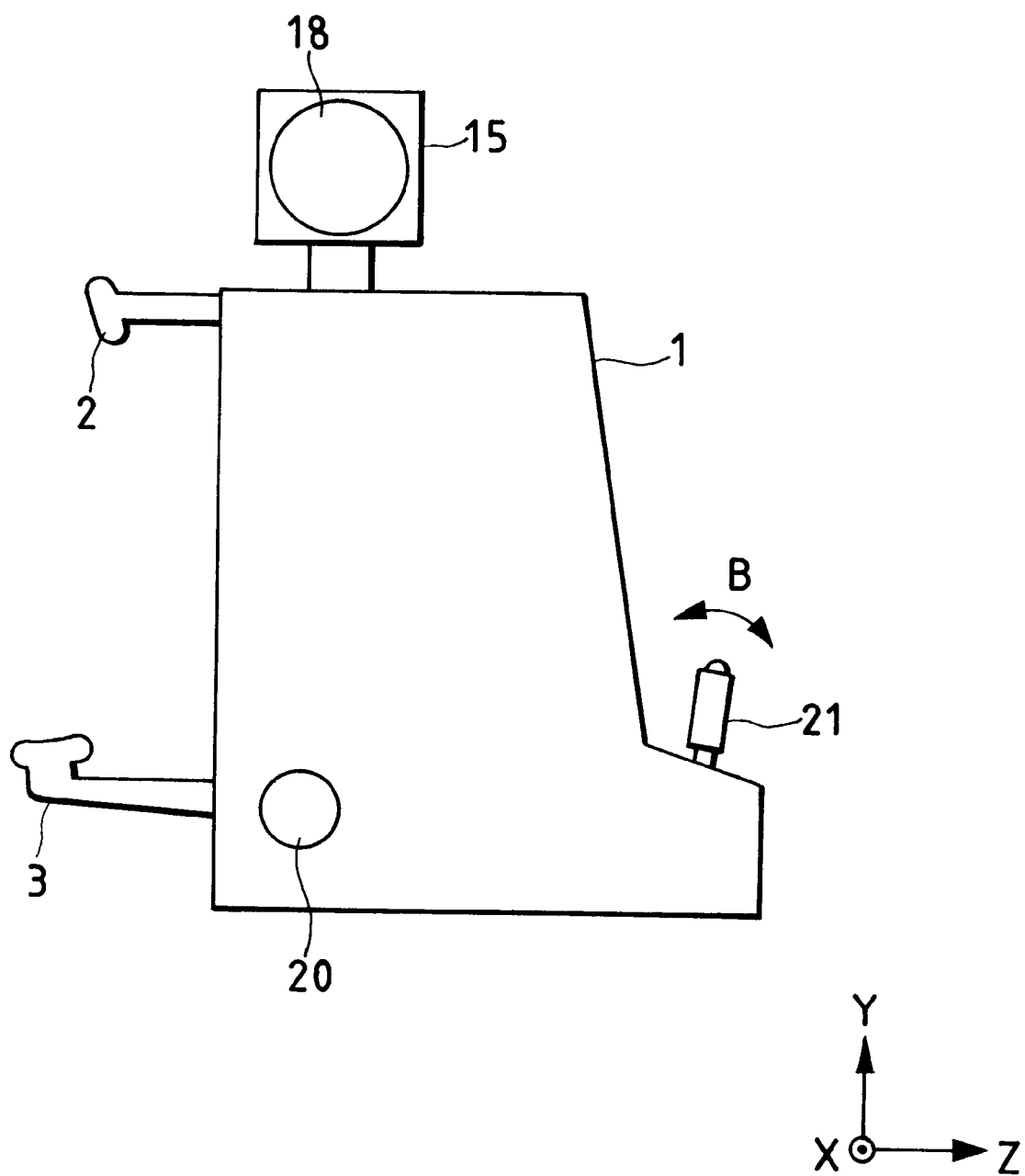

EYE EXAMINING APPARATUS HAVING A DRIVER FOR DRIVING AN EYE EXAMINING SYSTEM

This application is a continuation of application Ser. No. 08/378,579 filed Jan. 26, 1995, now abandoned.

BACKGROUND OF THE INVENTION

1. Field of the Invention

This invention relates to an eye examining apparatus for use in ophthalmic hospitals or optician's stores.

2. Related Background Art

Alignment for aligning an eye to be examined with the optical system of an eye examining apparatus has heretofore been effected by operating an operating rod mechanically connected to the sliding stand of the apparatus. At this time, an examiner operates the operating rod while observing a monitor screen displaying the image of the front eye part of the eye at a position opposed to an examinee with the apparatus interposed therebetween, but since the examiner is away from the examinee, it is difficult for the examiner to give close care to the examinee such as to raise his eyelashes, or to observe the fatigue of the examinee. For these purposes, it is preferable for the examiner to move near the examinee and effect adjustment or eye examination.

(1) However, it has been difficult for the examiner to move away from the location opposed to the examinee to be near the examinee on the examinee's side of the apparatus and perform the operation while observing the image of the front eye part on the monitor screen.

(2) Also, for the purpose of alignment, there has been proposed a method of providing an electronic viewfinder for observing the eye of the examinee, but this method suffers from the problem that the observation field will be lacking unless observation is made with the examiner's eye brought very close to the position of an eyepiece.

SUMMARY OF THE INVENTION

It is a first object of the present invention to provide an eye examining apparatus which an examiner can operate the apparatus at preferable positions.

It is a second object of the present invention to provide an eye examining apparatus which the examiner can operate in an easy posture.

Other objects of the present invention will become apparent from the following detailed description of some embodiments of the invention.

DESCRIPTION OF THE DRAWINGS

FIG. 2 shows the construction of a second embodiment of the present invention.

DESCRIPTION OF THE PREFERRED EMBODIMENTS

Figure 1:
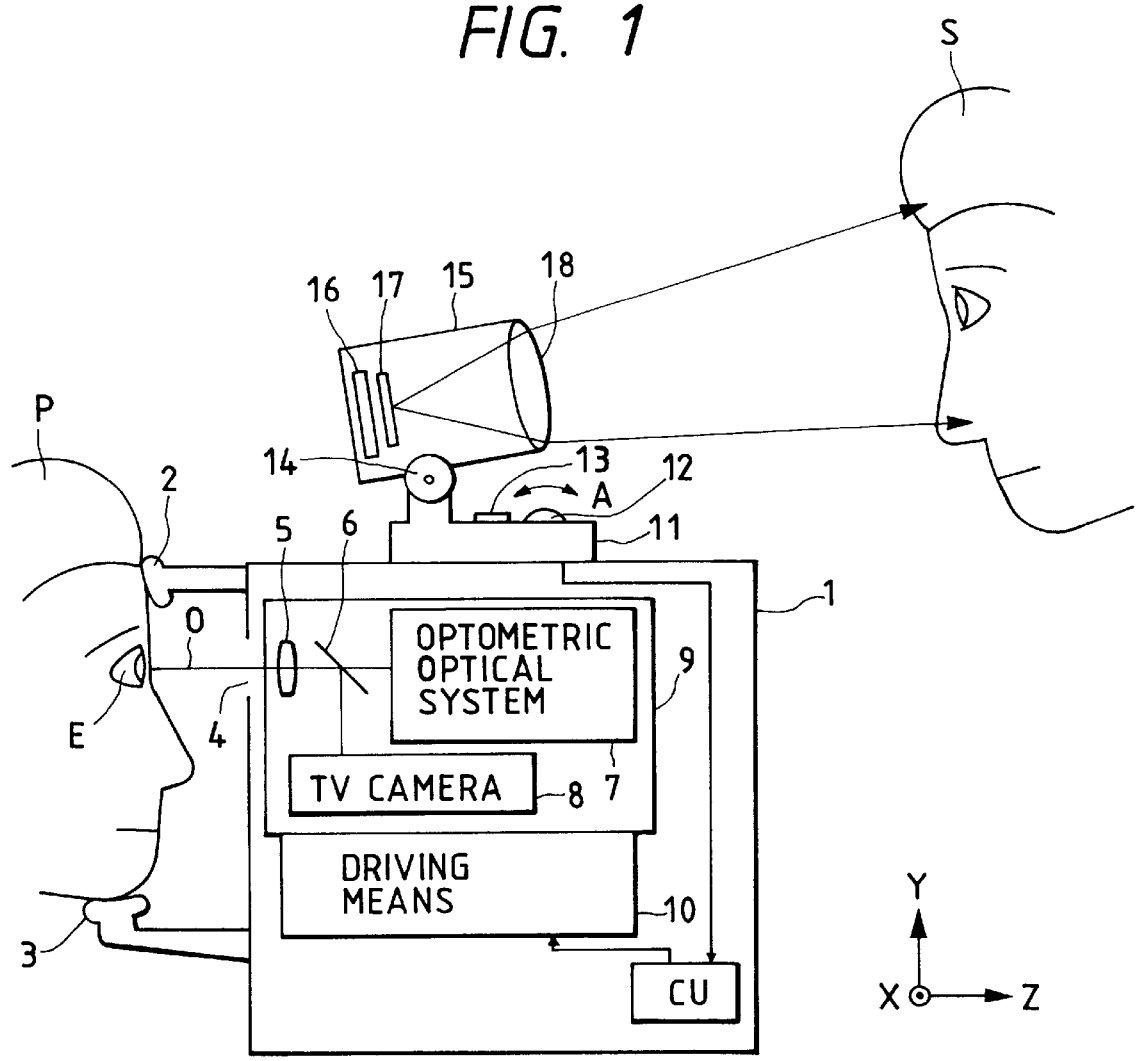
FIG. 1 shows the construction of a first embodiment of the present invention.

The invention will hereinafter be described in detail with respect to the embodiments thereof shown in the drawings.

Referring to FIG. 1 which shows a first embodiment of the present invention, a forehead pad 2 and a chin receiver 3 for fixing a head are provided on that surface of an apparatus body 1 which is adjacent to an examinee P, and a window 4 opens near an eye E to be examined Within the apparatus body 1 through the window 4, a lens 5, a dichroic mirror 6 and an optometric optical system 7 are arranged on an optical axis 0, and a TV camera 8, as an electronic imaging means, is disposed in the direction of reflection of the dichroic mirror 6. The lens 5, the dichroic mirror 6, the optometric optical system 7 and the TV camera 8 together constitute an eye examining unit 9, on which is mounted driving means 10 such as a stepping motor which is movable in three-dimensional directions for aligning the apparatus body with the eye E. The eye examining unit 9 is, for example, a known retinal camera, an eye refractometer or the like.

Also, a rotatable stand 11 rotatable in a horizontal plane about a vertical axis is mounted on the upper surface of the apparatus body 1, and a track ball 12 and a vertically moving switch 13 are provided on the rotatable stand 11. Display means 15 is mounted on the rotatable stand 11 with a joint 14 interposed therebetween, and this display means 15 is comprised of a liquid crystal display plate 17, a back light 16 and a lens 18.

CU designates a control unit for controlling the driving means 10 on the basis of input signals from the track ball 12 and the vertically moving switch 13. A signal from a rotatable stand rotated position detecting means, not shown, is also inputted to the control unit CU.

The control of the driving means 10 by the control unit CU when the rotatable stand 11 is in the position as shown in FIG. 1 is as follows. The track ball 12 on the rotatable stand 11 is rotated in the direction of arrow A, whereby the eye examining unit 9 is moved in the Z-direction along the optical axis 0, and when the track ball 12 is rotated in a direction perpendicular to the plane of the drawing sheet of FIG. 1, the eye examining unit 9 is moved to right and left, i.e., in X-direction, relative to the examinee P, and the movement in a vertical direction, i.e., Y-direction, is effected by the operation of the vertically moving switch 13. On the other hand, the display means 15 can have its elevation angle changed by the joint 14 to thereby vertically adjust the direction of its screen. Also, the rotatable stand 11 can be freely rotated with its central portion as the axis to thereby turn the display surface of the display means 15 laterally.

The head of the examinee P is fixed by the forehead pad 2 and the chin receiver 3, and an examiner S operates the track ball 12 and the vertically moving switch 13 to move the eye examining unit 9 by the driving means 10 so as to align the visual axis of the eye E to be examined with the optical axis 0 of the optometric optical system 7.

A beam of light from the optometric optical system 7 is transmitted through the dichroic mirror 6 and the lens 5 and irradiates the eye E to be examined. The reflected light from the eye E to be examined is reflected by the dichroic mirror 6 via the lens 5 and is imaged on the TV camera 8, and is displayed as the image of the front eye part of the eye E to be examined and/or the image of the fundus of the eye on the liquid crystal display plate 16 of the display means 15. The examiner S observes the image enlarged through the lens 18 and effects alignment and measurement.

When the rotatable stand 11 is rotated to turn the display means 15 laterally, the examiner S operates the apparatus from a lateral position while observing the image of the eye to be examined on the display surface, the control of the driving means 10 by the control unit CU which has recognized this rotation is changed over as follows. The track ball 12 on the rotatable stand 11 rotates with the display means 15 and therefore, when the track ball 12 is rotated in the direction perpendicular to the plane of the drawing sheet of FIG. 1, the eye examining unit 9 may be moved in X-direction, and when the track ball 12 is rotated to right and left (in the direction of arrow A), the eye examining unit 9 may be moved in Z-direction. Thus, the direction in which the apparatus moves and the direction of operation coincide with each other. Accordingly, there will be no feeling of physical disorder even if the examiner S operates the device while standing laterally of the apparatus body 1, and the examiner can readily take care of the examinee P to raise his or her eyelashes or the like beside the examinee P. Also, since the operating portion on the rotatable stand 11 moves with the display means 15, the operater can operate the apparatus at any position.

The distance from the display plate 16 to the magnifying lens 18 is made smaller than the focal length of the lens 18. A beam of light emitted from a point on the display plate 16 diverges by the lens 18 and becomes capable of being observed from a wide angle, and a convex lens is used as the lens 18 and therefore, the lens 18 has a magnifying action as well. Further, if the size of the lens 18 is made larger than the width of the eyes, it will be easy to see both eyes, and a virtual image will be formed at a finite distance farther than the display plate 16 and therefore, it will be possible for the examiner S to bring his face close to the apparatus and see a large image.

Referring now to FIG. 2 which shows the construction of a second embodiment of the present invention, the same reference numerals as those in FIG. 1 designate functionally similar members, and the eye examining unit 9, the driving means 10 and the control unit CU within the apparatus body 1 are not shown in FIG. 2. Also, the display means 15 is rotatable like that in FIG. 1. In the case of FIG. 2, the display means 15 is shown as being turned laterally. In this second embodiment, the design is such that the rotated position of the display means 15 is detected by detecting means, not shown, and the direction of the movement of the eye examining unit 9 is automatically changed over by the internal circuit of the control unit CU.

In the present embodiment, the device also includes a knob 20 for adjusting the level of the chin receiver 3 and further, an operating rod 21, is provided instead of the track ball 12 of FIG. 1, so that a face-to-face operation and lateral operation can be performed as in FIG. 1.

When the operating rod 21 is moved in the direction of arrow B in the plane of the drawing sheet of FIG. 2, if the display means 15 is set for lateral operation, that is, if the display means 15 is turned laterally as shown in FIG. 2, the eye examining unit 9 will be moved in the X-direction, and if the display means 15 is set for face-to-face operation, that is, if the display means 15 is turned in the same direction as that shown in FIG. 1, the eye examining unit 9 will be moved in the Z-direction, and thus, the movement of the image on the display means 15 and the movement of the operating rod 21 will coincide with each other. Likewise, when the operating rod 21 is moved perpendicularly to the plane of the drawing sheet of FIG. 2, in the case of the lateral operation, the eye examining unit 9 will be moved in the Z-direction, and in the case of face-to-face operation, it will be moved in the X-direction.

As described above, in the eye examining apparatus of the second embodiment, the direction of movement of the image of the eye to be examined on the display surface of the display means and the direction of operation of the operating means by the examiner are brought into coincidence with each other, whereby there is no feeling of perceptional confusion even for an operation at the lateral position of the examinee. There is little chance for an improper operation to take place.

Also, in the eye examining apparatus of the above-described embodiment, the magnifying convex lens is disposed so that the display surface of the display means may lie inside of the focal length thereof, whereby a virtual image is formed far away from the display surface and therefore, the examiner can perform observation with his face brought close to the apparatus and also, observation is possible from a wide range of angular directions and thus, the examiner can make observation in a free posture further, since an enlarged image is observed, a small display plate can be used and the eye examining apparatus can be made compact and the manufactured inexpensively.

What is claimed is:

1. An eye examining apparatus comprising:

an eye examining system provided with image pickup means for pickup up the image of an eye to be examined and for examining the eye to be examined;

driving means for driving said eye examining system;

input means for permitting an operator to effect an input operation in order to operate said driving means;

display means for displaying the image of the eye to be examined obtained by said image pickup means; and control means for changing the direction in which said driving means drives said eye examining system in accordance with the direction in which said input means is moved to effect the input operation in accordance with a change in a direction in which said display means faces.

2. The apparatus according to claim 1, wherein said control means executes said changing operation so that the direction in which said input means is moved to effect the input operation and the direction of movement of the eye to be examined displayed by said display means are brought into coincidence with each other regardless of the direction in which said display means faces.

3. The apparatus according to claim 1, wherein said apparatus has a body, and wherein said display means is horizontally rotatably provided on the upper portion of said body of the apparatus.

4. The apparatus according to claim 1, wherein said input means is a track ball.

5. The apparatus according to claim 1, wherein said input means is a joy stick.

6. The apparatus according to claim 1, herein said display means is capable of changing its angle in a vertical direction.

7. The apparatus according to claim 1, wherein said display means has a display plate and a lens system having a magnifying function.

8. The apparatus according to claim 1, wherein said driving means drives said eye examining system in a direction opposed to the eye to be examined and a horizontal direction perpendicular to said opposed direction in conformity with the input to said input means.

9. An eye examining apparatus comprising:

an eye examining system for electro-optically examining an eye to be examined including electronic imaging means for imaging the eye;

driving means for driving said eye examining system for aligning said eye examining system with the eye to be examined;

a main body including said eye examining system and said driving means; and an operation and display portion including input means for operating said driving means and display means mechanically connected with said input means and displaying the image of the eye by said electronic imaging means, said operation and display portion being arranged to be movable as a unit with respect to the main body, and wherein said display means is rotatable vertically with respect to said input means.

10. An apparatus according to claim 9, wherein an input portion of said input means of said operation and display portion is rotatably movable with respect to said main body.

11. An apparatus according to claim 9, wherein said input means has a track ball.

12. An apparatus according to claim 9, wherein said input means and said display means are mechanically connected so that said input means and said display means can be mutually displaced.

13. An eye examining apparatus comprising:

an eye examining system for examining an eye to be examined including an image pick-up element for picking-up an image of the eye to be examined;

a driving system for driving said eye examining system for aligning said eye examining system with the eye to be examined;

a main body including said eye examining system and said driving system;

an operation unit including at least one operation input element for permitting an operator to effect an input operation in order to operate said driving system and a display for displaying the image of the eye to be examined picked-up by said image pick-up element, said operation unit being arranged so that said at least one operation input element and said display are movable as a unit with respect to said main body, and wherein said display means is rotatable vertically with respect to said input means.

14. An apparatus according to claim 13, wherein said display and said operation input element are mechanically connected so that said display and said operation input element can be mutually displaced.

15. An eye examining apparatus comprising:

an eye examining system for examining an eye to be examined including an image pick-up element for picking-up an image of the eye to be examined;

a driving system for driving said eye examining system for aligning said eye examining system with the eye to be examined;

a main body including said eye examining system and said driving system;

a display for displaying the image of the eye to be examined picked-up by said image pick-up element, said display being arranged to be movable with respect to said main body; and an operation input system for permitting an operator to effect an input operation in order to operate said driving system, said operation input system being constructed so that the relation between the direction of movement of the image displayed by said display, caused by the driving of said eye examining system, and the direction of the input operation is unchanged before and after a movement of said display with respect to the main body.

16. An apparatus according to claim 15, wherein said operation input system includes an input member operatable by an operator and disposed in said main body of said operation input system.

17. An apparatus according to claim 16, further comprising operation input system control means for changing the relationship between the direction of an input operation using said input member and the direction of driving of said driving system according to the motion of said display.

18. An apparatus according to claim 16, wherein said input member is an operational rod and the input operation is directed to moving said operational rod.

19. An apparatus according to claim 15, wherein said display is rotatably moved with respect to said main body.

* * * * *

UNITED STATES PATENT AND TRADEMARK OFFICE
CERTIFICATE OF CORRECTION

PATENT NO. : 5,903,336

DATED : May 11, 1999

INVENTOR(S) : YOSHIMI KOHAYAKAWA

It is certified that error appears in the above-identified patent and that said Letters Patent is hereby corrected as shown below:

COLUMN 1

Line 66, "examined" should read --examined.--.

COLUMN 4

Line 44, "herein" should read --wherein--.

COLUMN 5

Line 23, "system;" should read --system; and--.

Signed and Sealed this

Ninth Day of November, 1999

Attest:

Q. TODD DICKINSON

Attesting Officer

Acting Commissioner of Patents and Trademarks